US00PP23852P2

(12) United States Plant Patent
Arts

(10) Patent No.: US PP23,852 P2
(45) Date of Patent: Aug. 27, 2013

(54) ***HYDRANGEA* PLANT NAMED 'AGRIHYDRAVIJFTIEN'**

(50) Latin Name: *Hydrangea hybrida*
Varietal Denomination: Agrihydravijftien

(75) Inventor: Niels Arts, Aalsmeer (NL)

(73) Assignee: Agriom, De Kwakel (NL)

( * ) Notice: Subject to any disclaimer, the term of this patent is extended or adjusted under 35 U.S.C. 154(b) by 122 days.

(21) Appl. No.: 13/200,602

(22) Filed: Sep. 24, 2011

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — June Hwu
(74) *Attorney, Agent, or Firm* — C. A. Whealy

(57) ABSTRACT

A new and distinct cultivar of *Hydrangea* plant named 'Agrihydravijftien', characterized by its upright and somewhat outwardly spreading plant habit; vigorous growth habit; strong and sturdy stems; freely flowering habit with numerous sterile flowers per inflorescence; large lacecap inflorescences with white-colored flowers with light red-colored margins; and short production time as a cooling treatment is not required for flower development.

1 Drawing Sheet

Botanical designation: *Hydrangea hybrida*.
Cultivar denomination: 'AGRIHYDRAVIJFTIEN'.

BACKGROUND OF THE INVENTION

The present invention relates to a new and distinct cultivar of *Hydrangea* plant, botanically known as *Hydrangea hybrida* and hereinafter referred to by the name 'Agrihydravijftien'.

The new *Hydrangea* plant is a product of a planned breeding program conducted by the Inventor in Aalsmeer, The Netherlands. The objective of the breeding program was to create new freely branching *Hydrangea* plants with strong and sturdy stems, large inflorescences, attractive flower color and not requirement for a cooling treatment for flower development.

The new *Hydrangea* plant originated from a cross-pollination made by the Inventor on Apr. 20, 2005 in De Kwakel, The Netherlands, of a proprietary selection of *Hydrangea hybrida* identified as code number 200126-03, not patented, as the female, or seed, parent with a proprietary selection of *Hydrangea hybrida* identified as code number 201164-04, not patented, as the male, or pollen, parent. The new *Hydrangea* plant was discovered and selected by the Inventor as a single flowering plant from within the progeny of the stated cross-pollination in a controlled greenhouse environment in Glandorf, Germany on Mar. 15, 2009.

Asexual reproduction of the new *Hydrangea* plant by vegetative cuttings in a controlled environment in Glandorf, Germany since Mar. 15, 2010 has shown that the unique features of this new *Hydrangea* plant are stable and reproduced true to type in successive generations.

SUMMARY OF THE INVENTION

Plants of the new *Hydrangea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Agrihydravijftien'. These characteristics in combination distinguish 'Agrihydravijftien' as a new and distinct *Hydrangea* plant:

1. Upright and somewhat outwardly spreading plant habit.
2. Vigorous growth habit.
3. Strong and sturdy stems.
4. Freely flowering habit with numerous sterile flowers per inflorescence.
5. Large lacecap inflorescences with white-colored flowers with light red-colored margins.
6. Short production time as a cooling treatment is not required for flower development.

Plants of the new *Hydrangea* can be compared to plants of the female parent selection. Plants of the new *Hydrangea* differ from plants of female parent selection primarily in the following characteristics:

1. Plants of the new *Hydrangea* have stronger branches than plants of the female parent selection.
2. Plants of the new *Hydrangea* and the female parent selection differ in sterile flower color as plants of the female parent selection have white-colored sterile flowers with red-colored margins.

Plants of the new *Hydrangea* can be compared to plants of the male parent selection. Plants of the new *Hydrangea* differ from plants of male parent selection primarily in sterile flower color as plants of the male parent selection have light pink-colored sterile flowers with red-colored margins.

Plants of the new *Hydrangea* can be compared to plants of the *Hydrangea hybrida* 'Agrihydrazeven', disclosed in U.S. Plant Pat. No. 19,737. Plants of the new *Hydrangea* differ from plants of 'Agrihydrazeven' in the following characteristics:

1. Plants of the new *Hydrangea* are shorter than plants of 'Agrihydrazeven'.

2. Plants of the new *Hydrangea* and 'Agrihydrazeven' differ in sterile flower color as plants of 'Agrihydrazeven' have white-colored sterile flowers without red-colored margins.

BRIEF DESCRIPTION OF THE PHOTOGRAPH

The accompanying colored photograph illustrates the unique appearance of the new *Hydrangea* plant showing the colors as true as it is reasonably possible to obtain in colored reproductions of this type. Colors in the photograph may differ from the color values cited in the detailed botanical description which accurately describe the colors of the new *Hydrangea* plant. The photograph comprises a side perspective view of a typical flowering plant of 'Agrihydravijftien' grown in a container.

DETAILED BOTANICAL DESCRIPTION

Plants used in the aforementioned photograph and in the following description were grown during the winter in 15-cm containers in a glass-covered greenhouse in De Kwakel, The Netherlands and under environmental conditions and cultural practices which closely approximate commercial *Hydrangea* production conditions. During the production of the plants, day and night temperatures averaged 17° C. Plants of the new *Hydrangea* were one year old when the photograph and description were taken. In the following description, color references are made to The Royal Horticultural Society Colour Chart, 1995 Edition, except where general terms of ordinary dictionary significance are used.

Botanical description: *Hydrangea hybrida* 'Agrihydravijftien'.

Parentage:

*Female, or seed, parent*.—Proprietary selection of *Hydrangea hybrida* identified as code number 200126-03, not patented.

*Male, or pollen, parent*.—Proprietary selection of *Hydrangea hybrida* identified as code number 201164-04, not patented.

Propagation:

*Type cutting*.—By vegetative cuttings.

*Time to initiate roots, summer*.—About two weeks at temperatures of 23° C.

*Time to initiate roots, winter*.—About 18 days at temperatures of 18° C.

*Time to produce a rooted young plant, summer*.—About four weeks at temperatures of 23° C.

*Time to produce a rooted young plant, winter*.—About five weeks at temperatures of 18° C.

*Root description*.—Thick; whitish brown in color.

*Rooting habit*.—Freely branching; dense.

Plant description:

*Plant and growth habit*.—Upright to somewhat outwardly spreading plant habit; rounded in shape; strong and sturdy stems; rapid growth rate and vigorous growth habit.

*Plant height*.—About 25 cm to 35 cm.

*Plant diameter or area of spread*.—About 40 cm.

Lateral branch description:

*Branching habit*.—Freely branching habit with about six lateral branches per plant.

*Length*.—About 25 cm.

*Diameter*.—About 5 mm to 6 mm.

*Internode length*.—About 5 cm to 7 cm.

*Stem texture*.—Smooth, glabrous.

*Strength*.—Strong and sturdy.

*Color*.—Close to 146C; at the nodes, close to 187A; lenticels, close to 184A.

Foliage description:

*Arrangement*.—Opposite, simple.

*Length*.—About 12.5 cm.

*Width*.—About 9 cm to 10 cm.

*Shape*.—Ovate.

*Apex*.—Acute to acuminate.

*Base*.—Obtuse.

*Margin*.—Slightly dentate.

*Texture, upper surface*.—Smooth to rugose, glabrous.

*Texture, lower surface*.—Rugose, glabrous.

*Venation pattern*.—Pinnate.

*Color*.—Developing leaves, upper surface: Close to 139A. Developing leaves, lower surface: Close to 137D. Fully expanded leaves, upper surface: Close to 139A; venation, close to 146D. Fully expanded leaves, lower surface: Close to 138D; venation, close to 146D.

*Petiole*.—Length: About 2 cm to 3 cm. Diameter: About 3.5 mm. Texture, upper and lower surfaces: Smooth, glabrous. Color, upper and lower surfaces: Close to 146D.

Flower description:

*Flower type and habit*.—Single rounded sterile and star-shaped fertile flowers arranged on terminal panicles; panicles globular in shape; flowers face upright to outwardly.

*Fragrance*.—None detected.

*Natural flowering season*.—Short production time as a cooling treatment is not required for flower development; continuous flowering during the summer in Northern Europe.

*Flower longevity*.—Sterile flowers last about four months on the plant, sterile flowers persistent; fertile flowers last about four weeks on the plant, fertile flowers not persistent.

*Quantity of flowers*.—Freely flowering habit; about 35 to 40 sterile flowers per panicle and about 120 fertile flowers per panicle.

*Panicle height*.—About 6 cm to 8 cm.

*Panicle diameter*.—About 17 cm.

*Sterile flower diameter*.—About 5 cm to 6 cm.

*Sterile flower depth (height)*.—About 5 mm.

*Fertile flower diameter*.—About 5 mm.

*Fertile flower depth (height)*.—About 5 mm.

*Petals, fertile flowers only, sterile flowers without petals*.—Quantity and arrangement: About five in a single whorl. Length: About 3.5 mm. Width: About 2 mm. Shape: Ovate. Apex: Acute. Base: Attenuate. Margin: Entire. Texture, upper and lower surfaces: Smooth, glabrous. Color: When opening, upper and lower surfaces: Close to 150D. Fully opened, upper and lower surfaces: Close to 155D; color does not fade with development.

*Sepals, sterile flowers*.—Quantity and arrangement: About four in a single whorl. Length: About 2.8 cm. Width: About 3 cm. Shape: Roughly deltoid. Apex: Retuse. Base: Cuneate. Margin: Entire. Texture, upper surface: Smooth, glabrous. Texture, lower surface: Smooth to rugose, glabrous. Color: When opening and fully opened, upper surface: Close to 155B; at the margins, close to 55A. When opening and fully opened, lower surface: Close to 155B.

*Sepals, fertile flowers*.—Quantity and arrangement: About four in a single whorl. Length: About 3.5 mm. Width: About 2 mm. Shape: Ovate. Apex: Acute. Base: Obtuse. Margin: Entire. Texture, upper and lower surfaces: Smooth, glabrous. Color, upper and lower surfaces: Close to 155B and 74B.

*Pedicels, sterile flowers*.—Length: About 2.5 cm. Diameter: About 1.5 mm. Strength: Strong. Texture: Smooth, glabrous. Color: Close to 155D and 65A.

*Pedicels, fertile flowers*.—Length: About 1.5 cm. Diameter: About 2 mm. Strength: Strong. Texture: Smooth, glabrous. Color: Close to 155D and 63D.

*Reproductive organs, fertile flowers only; sterile flowers without reproductive organs*.—Stamens: Quantity per flower: About eight. Anther shape: Conical. Anther length: About 1 mm. Anther color: Close to 74D. Pollen amount: Abundant. Pollen color: Close to 155D. Pistils: Pistil quantity per flower: About three. Pistil length: About 1 mm. Stigma shape: Oval. Stigma color: Close to 155C. Style length: About 1 mm. Style color: Close to 150D. Ovary color: Close to 150D.

*Seeds*.—Length: About 0.5 mm. Diameter: About 0.1 mm. Color: Close to 200C.

Disease/pest resistance: Under commercial production conditions, plants of the new *Hydrangea* have not been observed to be resistant to pathogens or pests common to *Hydrangea*.

Temperature tolerance: Plants of the new *Hydrangea* have been shown to be tolerant to temperatures ranging from about 3° C. to about 38° C.

It is claimed:

1. A new and distinct *Hydrangea* plant named 'Agrihydravijftien' as illustrated and described.

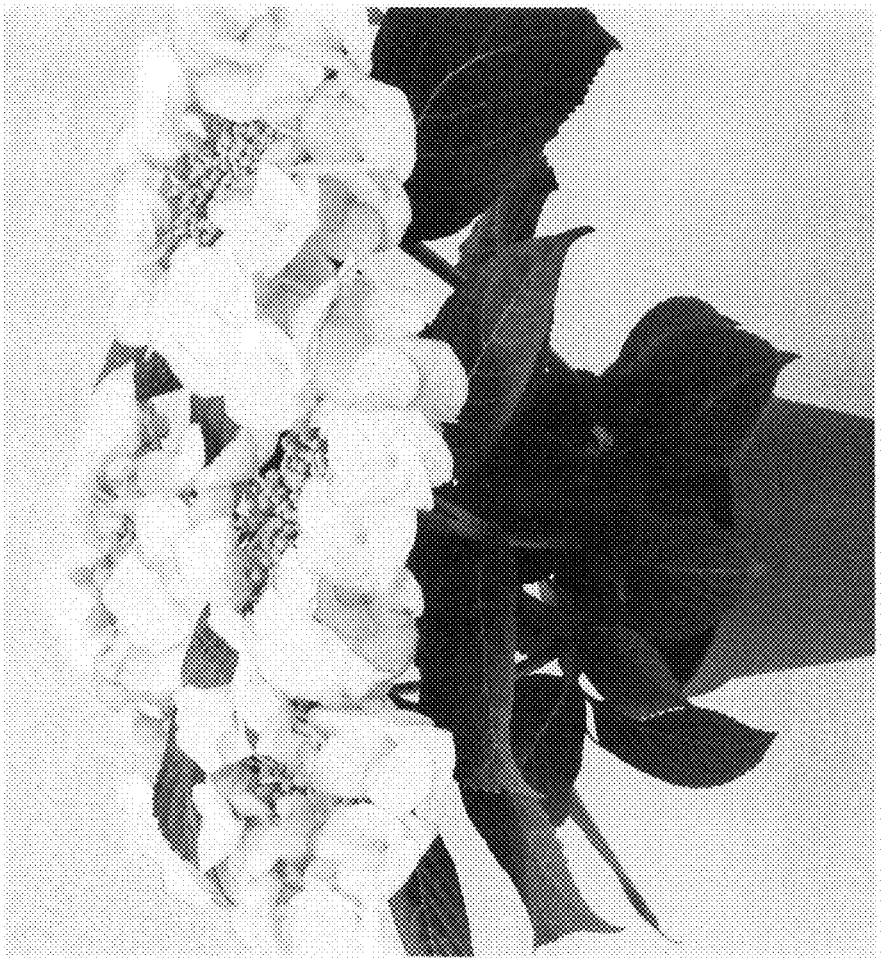

* * * * *